(12) United States Patent
Johnson et al.

(10) Patent No.: US 7,931,022 B2
(45) Date of Patent: Apr. 26, 2011

(54) METHOD AND APPARATUS FOR DISPENSING INHALATOR MEDICAMENT

(75) Inventors: Keith A. Johnson, Durham, NC (US); Robert A. Casper, Sanford, NC (US); David L. Gardner, Chapel Hill, NC (US)

(73) Assignee: Respirks, Inc., Raleigh, NC (US)

( * ) Notice: Subject to any disclaimer, the term of this patent is extended or adjusted under 35 U.S.C. 154(b) by 1663 days.

(21) Appl. No.: 10/267,013

(22) Filed: Oct. 8, 2002

(65) Prior Publication Data

US 2003/0075172 A1    Apr. 24, 2003

Related U.S. Application Data

(60) Provisional application No. 60/344,544, filed on Oct. 19, 2001.

(51) Int. Cl.
 *A61M 11/00*    (2006.01)

(52) U.S. Cl. .................. 128/203.15; 128/203.21

(58) Field of Classification Search ............. 128/203.12, 128/203.13, 203.15, 203.18, 203.19, 203.21, 128/203.23, 200.23; 604/58; 206/528, 530, 206/531, 532, 534.1, 534.2, 535, 536, 538, 206/539; 424/46, 489
See application file for complete search history.

(56) References Cited

U.S. PATENT DOCUMENTS

| | | | | |
|---|---|---|---|---|
| 4,295,567 A | * | 10/1981 | Knudsen | 206/534 |
| 4,627,432 A | * | 12/1986 | Newell et al. | 128/203.15 |
| 4,738,817 A | * | 4/1988 | Wittwer et al. | 264/328.14 |
| 4,778,054 A | * | 10/1988 | Newell et al. | 206/531 |
| 4,811,731 A | * | 3/1989 | Newell et al. | 128/203.15 |
| 5,002,048 A | * | 3/1991 | Makiej, Jr. | 128/200.23 |
| 5,035,237 A | * | 7/1991 | Newell et al. | 128/203.15 |
| 5,270,305 A | | 12/1993 | Palmer | |
| 5,349,947 A | * | 9/1994 | Newhouse et al. | 128/203.21 |
| 5,368,187 A | * | 11/1994 | Poncetta et al. | 221/30 |
| 5,415,162 A | | 5/1995 | Casper et al. | |
| 5,562,918 A | * | 10/1996 | Stimpson | 424/451 |
| 5,642,728 A | * | 7/1997 | Andersson et al. | 128/203.15 |
| 5,657,749 A | | 8/1997 | Cox | |
| 5,660,169 A | | 8/1997 | Källstrand et al. | |
| 5,674,860 A | | 10/1997 | Carling et al. | |
| 5,778,873 A | * | 7/1998 | Braithwaite | 128/203.15 |
| 5,830,490 A | * | 11/1998 | Weinstein et al. | 424/405 |
| 5,874,063 A | | 2/1999 | Briggner et al. | |
| 5,934,273 A | | 8/1999 | Andersson et al. | |
| 5,972,919 A | | 10/1999 | Carling et al. | |

(Continued)

FOREIGN PATENT DOCUMENTS

DE    44 00 084 A1    7/1995

(Continued)

OTHER PUBLICATIONS

A. Leff; Dose-response relationships in determining the safety:efficacy ratio; Respiratory Medicine (1997) 91 (Supplement A) 34-37; Chicago, USA.

(Continued)

*Primary Examiner* — Steven O Douglas
(74) *Attorney, Agent, or Firm* — Bateman IP Law Group

(57) ABSTRACT

An apparatus and method for delivering a plurality of medication includes providing first and second medicament on a medicament pack in separate containers for preventing either medicament from interfering with the stability of the other. In accordance with the method, the medicaments are preferably delivered in a single inhalation.

52 Claims, 13 Drawing Sheets

U.S. PATENT DOCUMENTS

| | | | |
|---|---|---|---|
| 5,980,949 A | 11/1999 | Trofast | |
| 5,983,956 A | 11/1999 | Trofast | |
| 6,027,714 A | 2/2000 | Trofast | |
| 6,030,604 A | 2/2000 | Trofast | |
| 6,065,472 A * | 5/2000 | Anderson et al. | 128/203.21 |
| 6,183,782 B1 | 2/2001 | Hallworth | |
| 6,221,398 B1 | 4/2001 | Jakupovic et al. | |
| 6,238,647 B1 | 5/2001 | Akehurst et al. | |
| 6,250,300 B1 | 6/2001 | Andersson et al. | |
| 6,287,540 B1 | 9/2001 | Trofast | |
| 6,288,118 B1 | 9/2001 | Nieman et al. | |
| 6,360,743 B1 | 3/2002 | Andersson et al. | |
| 6,516,796 B1 * | 2/2003 | Cox et al. | 128/200.23 |
| 6,536,427 B2 | 3/2003 | Davies et al. | |
| 6,537,524 B1 | 3/2003 | Hassan et al. | |
| 6,543,443 B1 * | 4/2003 | Klimowicz et al. | 128/200.23 |
| 6,555,583 B2 | 4/2003 | Nieman et al. | |
| 6,564,945 B1 * | 5/2003 | Weinstein et al. | 206/531 |
| 6,651,816 B2 * | 11/2003 | Weinstein | 206/534 |
| 6,667,344 B2 | 12/2003 | Banerjee et al. | |
| 6,679,254 B1 | 1/2004 | Rand et al. | |
| 6,698,425 B1 | 3/2004 | Widerstrom | |
| 6,810,874 B1 * | 11/2004 | Koskela et al. | 128/203.15 |
| 6,845,772 B2 * | 1/2005 | Braithwaite et al. | 128/203.15 |
| 6,866,037 B1 * | 3/2005 | Aslin et al. | 128/200.23 |
| 2002/0007869 A1 * | 1/2002 | Pui et al. | 141/173 |
| 2002/0066691 A1 * | 6/2002 | Varon | 206/534 |
| 2002/0103260 A1 | 8/2002 | Clarke et al. | |
| 2003/0026766 A1 | 2/2003 | Sanders | |
| 2003/0064031 A1 | 4/2003 | Humphrey et al. | |
| 2003/0064034 A1 | 4/2003 | Humphrey et al. | |
| 2003/0116157 A1 | 6/2003 | Braithwaite et al. | |
| 2004/0025874 A1 | 2/2004 | Seppala | |
| 2004/0025877 A1 | 2/2004 | Crowder et al. | |
| 2004/0035420 A1 | 2/2004 | Davies et al. | |

FOREIGN PATENT DOCUMENTS

| | | |
|---|---|---|
| GB | 2 264 237 | 5/1992 |
| WO | WO 97/02061 | 1/1997 |
| WO | PCT/US98/03799 | 3/1998 |
| WO | WO 98/34663 | 8/1998 |
| WO | WO 98/34664 | 8/1998 |
| WO | WO 99/21556 A1 * | 5/1999 |
| WO | WO 00/48587 | 8/2000 |
| WO | WO 01/17595 A1 * | 3/2001 |
| WO | WO 01/39823 A1 | 6/2001 |
| WO | WO 01/78735 A1 | 10/2001 |
| WO | WO 01/78745 A1 | 10/2001 |
| WO | PCT/IB02/03598 | 9/2002 |
| WO | WO 2004/012801 A1 | 2/2004 |
| WO | WO 2004/045487 | 3/2004 |

OTHER PUBLICATIONS

David J. Evans, M.B. et al.; A Comparison of Low-Dose Inhaled Budesonide Plus Theophylline and High-Dose Inhaled Budesonide for Moderate Asthma; The New England Journal of Medicine; Nov. 13, 1997; pp. 1412-1418; vol. 337 No. 20; London, UK.

* cited by examiner

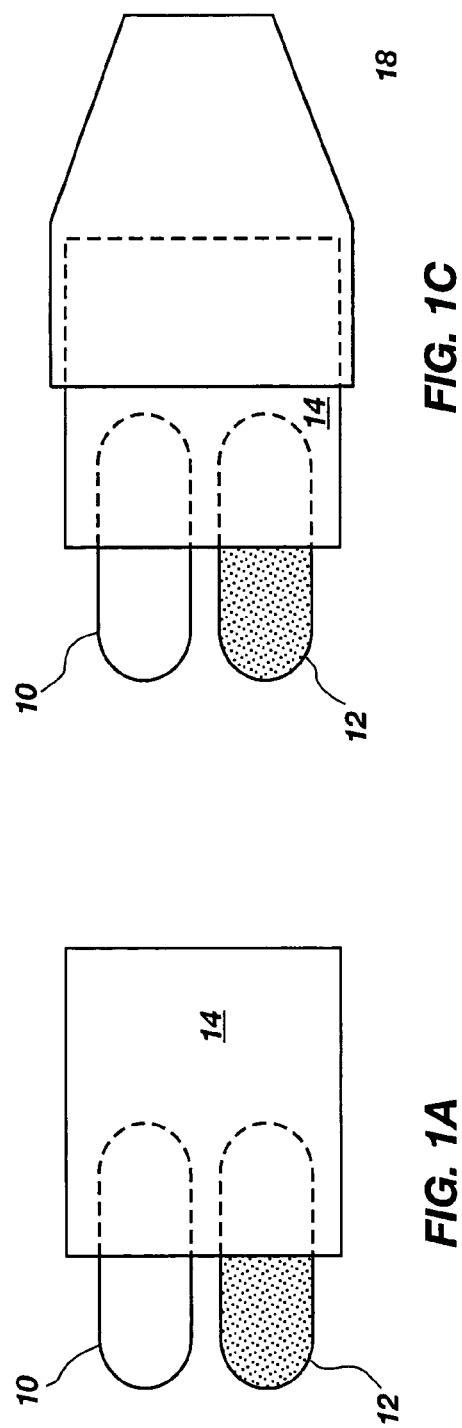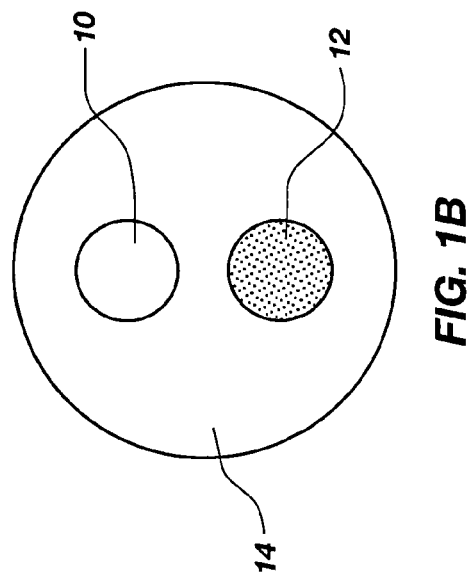

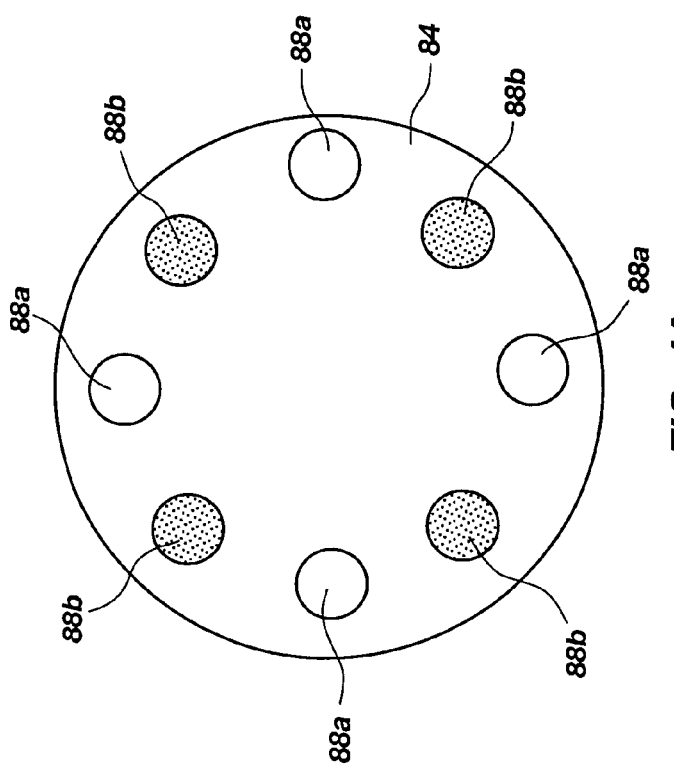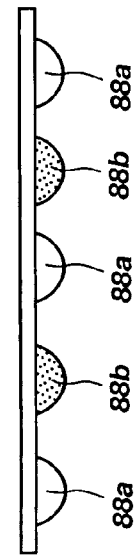

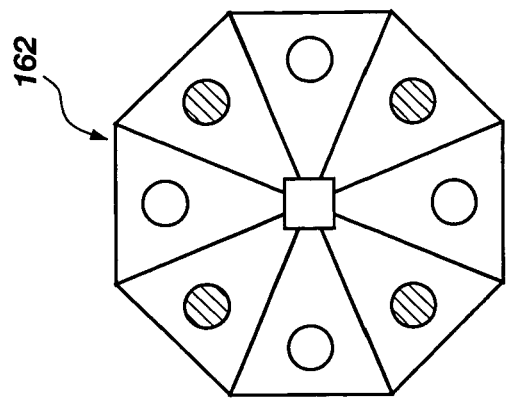
FIG. 11B
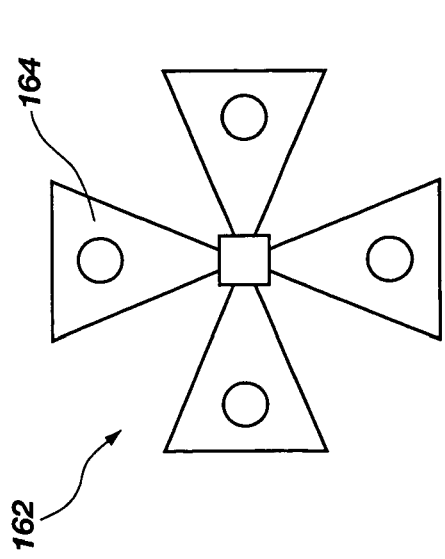
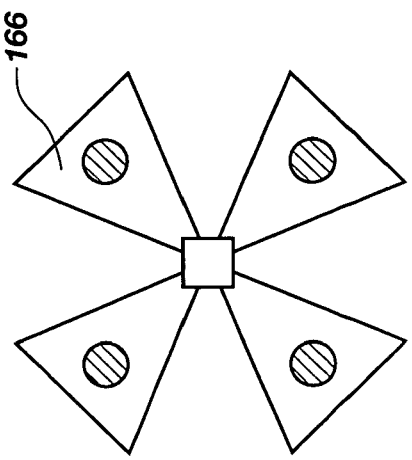
FIG. 11A

METHOD AND APPARATUS FOR DISPENSING INHALATOR MEDICAMENT

RELATED APPLICATIONS

The present application claims the benefit of U.S. Provisional Patent Application Ser. No. 60/344,544, filed Oct. 19, 2001.

BACKGROUND OF THE INVENTION

1. Field of the Invention

The present invention relates to a drug delivery system for a combination of medicaments for use in inhalators for the treatment of respiratory, systemic and topical diseases, for gene therapy, for vaccine administration, and for administration of antigens and adjuvants (i.e. birth control). More particularly, the present invention relates to a drug delivery system for the use of a combination of therapeutic agents for the treatment of respiratory diseases, e.g., asthma of whatever type or genesis, including intrinsic (non-allergic) and extrinsic (allergic) chronic obstructive pulmonary, airways or lung disease (COPD, COAD or COLD), emphysema, bronchitis, acute lung injury (ALI), pneumoconiosis, acute respiratory distress syndrome (ARDS), cystic fibrosis (CF), allergic rhinitis and exacerbations of airways hyperactivity consequent to other drug therapy. Other combinations of medicaments for use in inhalators may be used to treat systemic or topical disorders including lung and other cancers, infectious diseases including influenza, diabetes, immuno-compromised diseases including acquired immune deficiency syndrome (AIDS), bone degenerative diseases including osteoporosis, neurological degenerative diseases, including Alzheimer's and Parkinson's disease, pain management, cardiovascular disease, obesity, hepatitis, dermatological diseases, arthritis, hypertension and neurological disorders including depression.

3. State of the Art

The majority of commercially available inhalators are used in the treatment of respiratory disorders, e.g., asthma. Asthma is a chronic disease that affects millions of people in the United States, and a much larger number around the world. Asthma is typically initiated by the inhalation of antigens (sensitive patients) but, in some patients, there is a poorly defined mechanism(s) resulting in asthma and which is not associated with an antigen. Asthma is a condition characterized by inflammation and bronchial airway constriction that obstructs the patient's ability to breathe, resulting in wheezing, coughing and tightness of the chest.

There are many different medications used for treating asthma. While some patients respond sufficiently well to one type of medication or another, it is common for moderate to severe asthmatics to use more than one medication. Typically, a corticosteroid, e.g., beclomethasone or its derivatives and solvates, is used to minimize asthma symptoms by decreasing the airway hyper-responsiveness and inflammation while a bronchodilator, e.g., albuterol or its salt, is used to increase lung function and reduce the incidence of bronchial constriction. However, due to the short-acting relief provided by the bronchodilator, i.e., the bronchodilator must be administered frequently, e.g., 4-6 times per day, which may result in poor patient compliance. Furthermore, the bronchodilator product is less suitable for nocturnal asthma since it may not be effective through the duration of normal sleep.

Traditionally, the bronchodilator and steroidal product have been provided in separate medicament inhalators. For example, an inhalator may be used for the corticosteroid, while a separate inhalator is used for the bronchodilator. The use of two inhalers, however, has been found to be disadvantageous. Specifically, a patient using two inhalators increases the likelihood that the patient will fail to comply with the treatment protocol or may forget to take one of the medications.

Recently, more potent and/or longer-acting corticosteroids, e.g., fluticasone propionate, and beta2-agonist bronchodilator drugs, e.g., salmeterol and or its salt, have been developed. This has led to improved patient compliance, which can reduce emergency room visits and reduce the risks associated with nocturnal asthma.

In 1993, Glaxo Group Ltd. was issued U.S. Pat. No. 5,270,305 for a pharmaceutical composition comprising salmeterol (a long-acting beta2-agonist) and fluticasone propionate (steroid) as a combined preparation for the treatment of respiratory disorders, including the simultaneous, sequential or separate administration by inhalation via either a metered dose inhaler (MDI) or dry powder inhaler (DPI). This combination therapy had markedly greater efficiency and duration of bronchodilator action than previously known combinations. In addition, it permitted the establishment of a twice-daily dosing regimen with consequent substantial benefits in, for example, the treatment of asthma, particularly nocturnal asthma.

In 1997, Astra Aktiebolag was issued U.S. Pat. No. 5,674,860 for a combination product consisting of formoterol (long-acting beta2-agonist) and budesonide (steroid) for the treatment of mild as well as severe asthma and other respiratory disorders, including delivery via an MDI, DPI or nebulization. Additional patents covering combination products for the treatment of respiratory disease include U.S. Pat. Nos. 5,972,919, 6,030,604, and 6,183,782.

Recently, these combinations of the steroid and bronchodilator drugs have been commercialized in dry powder inhalers, i.e., ADVAIR® medicament in the DISKUS® dry powder inhalator, and SYMBICORT® medicament in the TURBUHALER® dry powder inhalator. It has been found that the use of the two medicaments together improved patient treatment. Additionally, requiring a patient to use a single inhalator increases the likelihood of patient compliance as the patient need only remember a more limited number of medicament applications.

It is evident from the above discussion that there is often a synergistic effect of a combination of drugs when the two drugs are administered together. It is likewise evident from the above discussion that the use of a single inhalator increases the likelihood of patient compliance as the patient need only remember a more limited number of medicament applications.

While combining medications is advantageous in some ways, it also raises concerns. Many medicaments are disposed on a carrier, such as lactose. While the carrier can be carefully selected to a particular medicament, the presence of multiple medicaments or multiple carriers may render the medicaments and/or carriers unstable. This, in turn, places limitations on the combinations of medicaments which can be used together. By eliminating the interaction of medicaments during storage, however, a broad range of medicaments can be administered substantially simultaneously.

It is therefore an object of the present invention to address the delivery of a combination of medicaments for the treatment of respiratory, systemic and topical diseases from dry powder inhalators (DPIs), such as the DPI device in U.S. Pat. No. 6,209,538 and other devices.

SUMMARY AND OBJECT OF THE INVENTION

It is an object of the present invention to provide an improved method of inhalation drug delivery for a combination of two or more medicaments.

It is another object of the present invention to provide such a method for treating respiratory and systemic diseases.

It is another object of the present invention to provide an apparatus for supplying two medicaments with a single inhalation.

The above and other objects of the present invention are achieved through a medicament packaging system and an inhalator for dispensing or dispersing the medicament combination. Each medicament formulation is prepared, filled, and sealed into separate container elements on the medicament package. The medicament container elements are arranged in the package so that only a container element of each medicament formulation is available for inhalation at one time when the package is integrated into the inhalator. The container elements are selected from the group such as, but not limited to, blisters, capsules, vials, ampules, tubes, pouches, bubble packs, or bottles all with appropriate closures. The dry powder medicament formulations combined as described above may be delivered in a single inspired breath either simultaneously or sequentially wherein the delivery system is comprised of a dry powder inhalator, with or without a "breath triggering" feature for providing control of medicament introduction into a patient's inspired air stream. However, because the medicaments are stored separately and are not mixed until the point of inhalation of shortly before, the risk of deterioration of one of the medicaments or carriers is virtually eliminated.

In accordance with one aspect of the present invention, one or more medicaments are selected from the group of brochodilators or prophylactic agents including, but not limited to, albuterol, albuterol sulfate, fenoterol hydrobromide, formoterol fumarate, metaproterenol sulfate, ipratropium bromide, tiotropium bromide, and sodium cromoglycate.

In accordance with another aspect of the present invention, one or more medicaments are selected from the group of steroids, androgens and glucocorticosteroid such as, but not limited to budesonide, beclomethasone dipropionate, fluticasone propionate, mometasone furoate, flunisolide, triamcinalone acetonide, dehydroepiandrosterone and its derivatives, and ciclesonide.

In accordance with yet another aspect of the present invention, one or more medicaments is selected from the group of compounds used to treat respiratory disorders including, but not limited to, synthetic or natural lung surfactant, alpha-1 antitrypsin, dornase alfa, poractant alfa, oligonucleotides, phosphodiesterase inhibitors, mast cell stabilizers, leukotriene antagonists, antihistamines, anti-IL4 and IL5 antagonists, neurokinin antagonists, anti-IgE monoclonal antibodies, VLA-4 antagonists, anti-L5 monoclonal antibodies, endothelin antagonists, tachkinin antagonists, elastase antagonist, integrin antagonists, retinoid agonists and adenosine agonists.

In accordance with still another aspect of the present invention, one or more medicaments is selected from the group of compounds used to diagnose respiratory ailments such as, but not limited to, sodium chloride and uridine 5'-triphosphate, methylcholine, and histamine.

In accordance with yet another aspect of the present invention, one or more medicaments are selected from the group of compounds that are typically administered orally or parenterally such as, but not limited to morphine and its salts, fentanyl and its salts, sufentanil and its salts, paclitaxel, vinorelbine and its salts, salmon calcitonin, parathyroid hormone, human growth hormone, interferons, insulin, lamivudine zidovudine, metformin hydrochloride, cefuroxime axetil, amoxicillin, ramipril, digoxin, zanamivir, oseltamivir and its salts, bupropion and its salts, citalopram and its salts, donepezil and its salts, amiloride and it salts, and rivastigmine and its salts.

In accordance with another aspect of the present invention, one or more of the medicament compounds has a size range substantially less than 10 microns.

In accordance with another aspect of the present invention, one or more of the medicament compounds has a size range substantially less than one micron.

In accordance with still another aspect of the present invention, one or more of the medicaments formulations are substantially free from a carrier or excipient.

In accordance with yet another aspect of the invention, the medicaments are present as agglomerates in the size range of 5 to 250 microns.

In accordance with another aspect of the present invention, one or more of the medicament formulations contain one or more carriers such as, but not limited to, lactose, glucose, raffinose, trehalose, mannitol, sorbitol or glycine.

In accordance with another aspect of the present invention, one or more of the medicaments are prepared as a microsphere or microcapsule with a suitable polymeric material so that the particle's size is substantially less than 10 microns. Microspheres or microcapsules could be used for immediate or sustained release of one or more medicaments in the lung.

BRIEF DESCRIPTION OF THE DRAWINGS

The above and other objects, features and advantages of the invention will become apparent from a consideration of the following detailed description presented in connection with the accompanying drawings in which:

FIG. 1A shows a side view of a medicament package formed in accordance with the principles of the present invention;

FIG. 1B shows an end view of the medicament package of FIG. 1A;

FIG. 1C shows a side view of the medicament package of FIG. 1A disposed in a mouthpiece;

FIG. 4A shows a top view of a blister pack disk formed in accordance with the principles of the present invention;

FIG. 4B shows a side view of the blister pack disk of FIG. 4A;

FIGS. 11A and 11B show an exploded view of yet another blister card in accordance with the present invention, and an assembled view of the same.

DETAILED DESCRIPTION

Figure 2A:
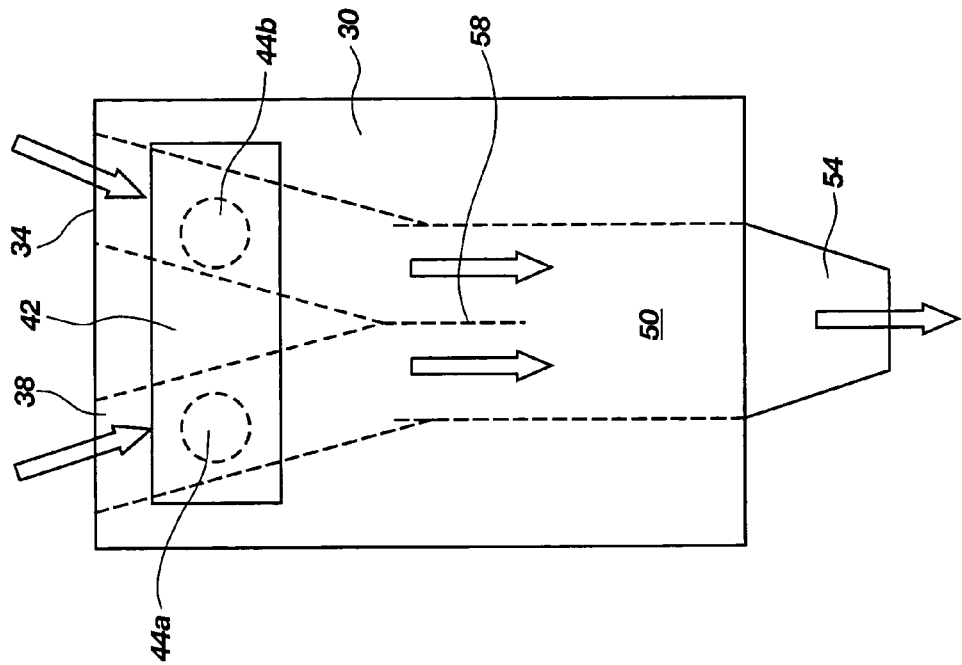
FIG. 2A shows a plan view of an inhalator made in accordance with the principles of the present invention at the beginning of an inhalation cycle.

The invention will now be described so as to enable one skilled in the art to make and use the invention. It is to be understood that the following description is only exemplary of the principles of the present invention and should not be viewed as narrowing the pending claims. It should further be understood that the various embodiments and examples relate to various aspects of the present invention, and not all embodiments need to achieve all objects of the invention.

In accordance with the present invention, it has been found that a relatively large number of medicaments can be combined in a dry powder inhalation drug delivery system to treat respiratory and systemic diseases. By placing the individual medicament powders within separate container elements in the same package and incorporating the package into a dry powder inhaler, with or without a "breath triggering" feature for providing control of medicament introduction into a patient's inspired air stream, the individual medicaments can be delivered simultaneously or sequentially with one inhalation by the patient, thus increasing the likelihood of compliance to achieve improved efficacy. Furthermore, by formulating, compounding, and filling each medicament compound into separate container elements; the excipients or carriers and manufacturing process can be optimized for each medicament powder's chemical stability, physical stability and fine particle mass following introduction into the air stream. This enables maximization of each medicament's shelf life and targeting to the lung.

EXAMPLE 1

A formulation of albuterol sulfate, with 99% of the particles being less than 10 microns, is prepared with an inhalation grade of lactose so that the ratio of albuterol base to lactose is 2:250 weight to weight. A second formulation of fluticasone propionate, with 99% of the particles being less than 10 microns, is prepared with an inhalation grade of lactose so that the ratio of drug to lactose is 2:250 weight to weight. Both formulations are packaged in different capsules with nominal fills of 50 mg of powder. The capsules are inserted into a dry powder inhalator and pierced. The respirable dose from a single inspiration, as measured by cascade impaction with a 4 second pulse at 60 L/min, is 25 micrograms and 62 micrograms for albuterol base and fluticasone propionate, respectively.

EXAMPLE 2

A formulation of formoterol fumarate, with 99% of the particles being less than 10 microns, is prepared with lactose, having a median particle size of 50-60 microns, so that the ratio of drug to lactose is 1:100 weight to weight. A second formulation of fluticasone propionate, with 99% of the particles being less than 10 microns, is prepared with lactose, having a median particle size of 70-80 microns, so that the ratio of drug to lactose is 1:100 weight to weight. Both formulations are packaged in different blisters that are incorporated on the same blister card. The blisters are arranged on the card so that only a single blister of each formulation is available for inhalation at one time. The triggering for the inhalation device is timed so that the formoterol fumarate formulation is introduced into the air stream before the fluticasone propionate formulation.

EXAMPLE 3

A formulation of formoterol fumarate, with 99% of the particles being less than 10 microns, is prepared with lactose, having a median particle size of 70-80 microns, so that the ratio of drug to lactose is 1:100 weight to weight. A second formulation of ipratropium bromide, with 99% of the particles being less than 5 microns, is prepared with lactose, having a median particle size of 70-80 microns, so that the ratio of drug to lactose is 1:100 weight to weight. Both formulations are packaged in separate sealed tubes that are incorporated on the inhalator. The tubes are arranged in the inhalator so that only a single tube of each formulation is available for inhalation at one time. The triggering for the inhalation device is timed so that both formulations are introduced into the air stream simultaneously.

EXAMPLE 4

A formulation of microencapsulated (as microspheres or microcapsules) ciclesonide, with 99% of the particles being less than 10 microns, is prepared with lactose, having a median particle size of 50-60 microns, so that the ratio of drug to lactose is 1:100 weight to weight. A second formulation of ipratropium bromide, with 99% of the particles being less than 10 microns, is prepared with trehalose, having a median particle size of 50-60 microns, so that the ratio of drug to lactose is 1:50 weight to weight. Both formulations are packaged in different blisters that are incorporated on the same blister card. The blisters are arranged on the card so that only a single blister of each formulation is available for inhalation at one time. The triggering for the inhalation device is timed so that the ipratropium bromide formulation is introduced into the air stream before the ciclesonide formulation.

EXAMPLE 5

A formulation of fentanyl citrate, with 99% of the particles being less than 5 microns, is prepared with lactose, having a median particle size of 5 microns, so that the ratio of drug to lactose is 50:50 weight to weight. A second formulation of sufentanil citrate, with 99% of the particles being less than 5 microns, is prepared with lactose, having a median particle size of 70-80 microns, so that the ratio of drug to lactose is 1:100 weight to weight. Both formulations are packaged in different blisters that are incorporated on the same blister card. The blisters are arranged on the card so that only a single blister of each formulation is available for inhalation at one time. The triggering for the inhalation device is timed so that both formulations are introduced into the air stream simultaneously.

EXAMPLE 6

A formulation of microencapsulated ciclesonide, with 99% of the particles being less than 10 microns, is prepared with lactose, having a median particle size of 50-60 microns, so that the ratio of drug to lactose is 1:100 weight to weight. A second formulation of microencapsulated triamcinalone acetonide, with 99% of the particles being less than 10 microns, is prepared with lactose, having a median particle size of 50-60 microns, so that the ratio of drug to lactose is 10:100 weight to weight. Both formulations are packaged in different vials that are incorporated in the inhalator. The vials are arranged in the inhalator so that only a single vial of each formulation is available for inhalation at one time. The triggering for the inhalation device is timed so that both formulations are introduced into the air stream simultaneously.

EXAMPLE 7

A formulation of paclitaxel, with 99% of the particles being less than 10 microns, is prepared with lactose, having a median particle size of 100-120 microns, so that the ratio of drug to lactose is 1:100 weight to weight. A second formulation of vinorelbine tartrate, with 99% of the particles being less than 10 microns, is prepared with lactose, having a median particle size of 50-60 microns, so that the ratio of drug to lactose is 10:100 weight to weight. Both formulations are packaged in different blisters that are incorporated on the same blister card. The blisters are arranged on the card so that only a single blister of each formulation is available for inhalation at one time. The triggering for the inhalation device is timed so that the vinorelbine tartrate formulation is introduced into the air stream before the paclitaxel formulation.

EXAMPLE 8

A formulation of salmon calcitonin, with 99% of the particles being less than 10 microns, is prepared with lactose, having a median particle size of 100-120 microns, so that the ratio of drug to lactose is 1:100 weight to weight. A second formulation of parathyroid hormone, with 99% of the particles being less than 10 microns, is prepared with lactose, having a median particle size of 50-60 microns, so that the ratio of drug to lactose is 10:100 weight to weight. Both formulations are packaged in different capsules that are incorporated in the inhalator. The capsules are arranged in the inhalator so that only a single capsule of each formulation is available for inhalation at one time. The triggering for the inhalation device is timed so that the salmon calcitonin formulation is introduced into the air stream before the parathyroid hormone formulation.

EXAMPLE 9

A formulation of lamivudine, with 99% of the particles being less than 10 microns, is prepared with lactose, having a median particle size of 100-120 microns, so that the ratio of drug to lactose is 1:100 weight to weight. A second formulation of zidovudine, with 99% of the particles being less than 10 microns, is prepared with lactose, having a median particle size of 50-60 microns, so that the ratio of drug to lactose is 10:100 weight to weight. A third formulation of interferon alfa-2b, with 99% of the particles being less than 10 microns, is prepared with lactose, having a median particle size of 50-60 microns, so that the ratio of drug to lactose is 10:100 weight to weight. The three formulations are packaged in different blisters that are incorporated on the same blister card. The blisters are arranged on the card so that only a single blister of each formulation is available for inhalation at one time. The triggering for the inhalation device is timed so that both formulations are introduced into the air stream simultaneously.

EXAMPLE 10

A formulation of insulin, with 99% of the particles being less than 10 microns, is prepared so that the drug particles form agglomerates or aggregates that are substantially between 10 and 200 microns. A second formulation of metformin hydrochloride, with 99% of the particles being less than 10 microns, is prepared with raffinose, having a median particle size of 50-60 microns, so that the ratio of drug to lactose is 10:100 weight to weight. Both formulations are packaged in different blisters that are incorporated on the same blister card. The blisters are arranged on the card so that only a single blister of each formulation is available for inhalation at one time. The triggering for the inhalation device is timed so that both formulations are introduced into the air stream simultaneously.

EXAMPLE 11

A formulation of cefuroxime axetil, with 99% of the particles being less than 10 microns, is prepared with mannitol, having a median particle size of 100-120 microns, so that the ratio of drug to lactose is 1:100 weight to weight. A second formulation of amoxicillin, with 99% of the particles being less than 10 microns, is prepared with glucose, having a median particle size of 50-60 microns, so that the ratio of drug to lactose is 10:100 weight to weight. Both formulations are packaged in different blisters that are incorporated on the same blister card. The blisters are arranged on the card so that only a single blister of each formulation is available for inhalation at one time. The triggering for the inhalation device is timed so that both formulations are introduced into the air stream simultaneously. Those skilled in the art will also appreciate, in light of the present disclosure, that the provision of two or more antibiotics on a blister pack would allow alternate antibiotic dosing. This, in turn, could be used to dramatically reduce the risk of antibiotic resistant bacteria from developing.

EXAMPLE 12

A formulation of ramipril, with 99% of the particles being less than 10 microns, is prepared with lactose, having a median particle size of 50-70 microns, so that the ratio of drug to lactose is 1:100 weight to weight. A second formulation of microencapsulated digoxin, with 99% of the particles being less than 10 microns, is prepared with raffinose, having a median particle size of 50-60 microns, so that the ratio of drug to lactose is 10:100 weight to weight. Both formulations are packaged in different blisters that are incorporated on the same blister card. The blisters are arranged on the card so that only a single blister of each formulation is available for inhalation at one time. The triggering for the inhalation device is timed so that both formulations are introduced into the air stream simultaneously.

EXAMPLE 13

A formulation of zanamivir, with 99% of the particles being less than 10 microns, is prepared with lactose, having a median particle size of 50-70 microns, so that the ratio of drug to lactose is 1:100 weight to weight. A second formulation of oseltamivir phosphate, with 99% of the particles being less than 5 microns, is prepared so that the drug content is 100% w/w. Both formulations are packaged in different blisters that are incorporated on the same blister card. The blisters are arranged on the card so that only a single blister of each formulation is available for inhalation at one time. The triggering for the inhalation device is timed so that the oseltamivir phosphate formulation is introduced into the air stream before the zanamivir formulation.

EXAMPLE 14

A formulation of zanamivir, with 99% of the particles being less than 5 microns, is prepared with glycine, having a median particle size of 50-70 microns, so that the ratio of drug to lactose is 1:100 weight to weight. A second formulation of oseltamivir phosphate, with 99% of the particles being less than 5 microns, is prepared so that the drug content is 100% w/w. Both formulations are packaged in different blisters that are incorporated on the same blister card. The blisters are arranged on the card so that only a single blister of each formulation is available for inhalation at one time. The triggering for the inhalation device is timed so that both formulations are introduced into the air stream simultaneously.

EXAMPLE 15

A formulation of bupropion hydrochloride, with 99% of the particles being less than 10 microns, is prepared so that the drug content is 100% w/w. A second formulation of citalopram hydrobromide, with 99% of the particles being less than 5 microns, is prepared so that the drug content is 100% w/w. Both formulations are packaged in different blisters that are incorporated on the same blister card. The blisters are arranged on the card so that only a single blister of each formulation is available for inhalation at one time. The triggering for the inhalation device is timed so that the bupropion hydrochloride formulation is introduced into the air stream before the citalopram hydrobromide formulation.

EXAMPLE 16

A formulation of donepezil hydrochloride, with 99% of the particles being less than 10 microns, is prepared with lactose, having a median particle size of 50-60 microns, so that the ratio of drug to lactose is 1:100 weight to weight. A second formulation of rivastigmine tartrate, with 99% of the particles being less than 10 microns, is prepared with lactose, having a median particle size of 70-80 microns, so that the ratio of drug to lactose is 1:100 weight to weight. Both formulations are packaged in different blisters that are incorporated on the same blister card. The blisters are arranged on the card so that only a single blister of each formulation is available for inhalation at one time. The triggering for the inhalation device is timed so that both formulations are introduced into the air stream simultaneously.

EXAMPLE 17

A formulation of gabapentenoid with 99% of the particles being less than 10 microns, is prepared so that the drug content is 100% by weight. A second formulation of naproxen, with 99% of particles being less than 5 microns is prepared so that the drug content is 100% by weight. Both formulations are packaged in different blisters that are incorporated on the same blister card. The blisters are arranged on the card so that only a single blister of each formulation is available for inhalation at a time. The triggering for the inhalation device is timed so that the gabapentenoid is introduced into the air stream before the naproxen.

EXAMPLE 18

A formulation of telmisartan, with 99% of the particles being less than 10 micron, is prepared so that the drug content is 100% by weight. A second formulation of lacidipine, with 99% of the particles being less than 5 microns, is prepared so that the drug content is 100% by weight. Both formulations are packaged in different blisters that are incorporated on the same blister card. The blisters are arranged on the card so that only a single blister of each formulation is available for inhalation at one time. The triggering for the inhalation device is timed so that the telmisartan is introduced into the air stream before the lacidipine.

The medicament formulations packaged according to the present invention can be delivered to the patient via any common inhaler, such as those with use blister packs or dispense bulk medicament. Furthermore, inhalers can be specially configured to control flow rates and when the medicaments are distributed to the user.

While the 18 examples above are typical; it should be appreciated that any of the drugs can be formulation, filled, and sealed in a blister package according to the present invention. The desired ratios of active drug in the medicament formulations will depend both on the particular medicament being used and on the medical needs of the patient.

As indicated above, the formulation can be used in traditional inhalers. In other words, the formulations can be dispensed from the single dose or multiple dose blister packs to increase the ease of use. Dose is defined as the amount of each medicament powder delivered with a single inhalation. Additionally, the formulations can be dispensed from a device in which the formulations are mixed with an air stream at a specific volumetric flow rate, thereby increasing the likelihood of deep lung targeting of one or more of the medicaments. An example of an inhalator providing such dispensing is discussed in U.S. Pat. No. 5,98,163. Propellant-based formulations can be delivered through an inhaler such as that described in U.S. Pat. No. 5,826,571 (Casper et al.).

Turning now to the drawings, there are shown numerous different configurations for supplying two different drugs to the user from a single device without the risk of the medicaments or their carriers interfering with the stability of the other. Furthermore, while discussed for simplicity as having two drugs, it will also be appreciated that the method of the present invention can involve three or more drugs being inhaled though a common inhaler.

FIGS. 1A, 1B and 1C show an embodiment wherein the medicament, packaged in a pair of capsules 10 and 12, is held in a medicament package 14. The capsules are disposed adjacent each other, but each capsule 10, 12 keeps the contents thereof from interfering with the contents of the other capsule. In use, the capsules 10, 12 are pierced or broken and the user inhales through the mouthpiece 18, thereby receiving the appropriate dose of two medications simultaneously.

FIG. 2A shows a plan view of an inhalator made in accordance with the principles of the present invention at the beginning of an inhalation cycle. The inhalator 30 includes a first inflow channel 34 and a second inflow channel 38. Each of the inflow channels are disposed in communication with a blister pack 42, with one bister 44a and 44b being disposed in communication with each inflow channel.

The first inflow channel 34 and the second inflow channel 38 are disposed in communication with an inhalation channel 50 which leads to a mouthpiece. While the first inflow channel 34 and the second inflow channel 38 can be disposed to allow simultaneous inhalation of the medicament in the blisters 44a and 44b, a flap 58 is disposed at the end of second inflow channel 38. The flap 58 initially inhibits airflow through the second inflow channel 38 caused by inhalation. Thus, inhalation initially draws medicament from the blister 44b in the first inhalation channel 34. As the inhalation draws the flap 58 open, the medicament in blister 44a is able to flow through the second inflow channel 38. Depending on the resistance of the flap 58 to opening, this can delay delivery of the medicament in blister 44a until after inhalation of the medicament in blister 44b is complete, or may only delay it momentarily. Additionally, the flap 58 helps to ensure sufficient inhalation rate is sufficient to increase the likelihood that the medicament will be delivered to the appropriate portion of the lung.

Figure 3A:
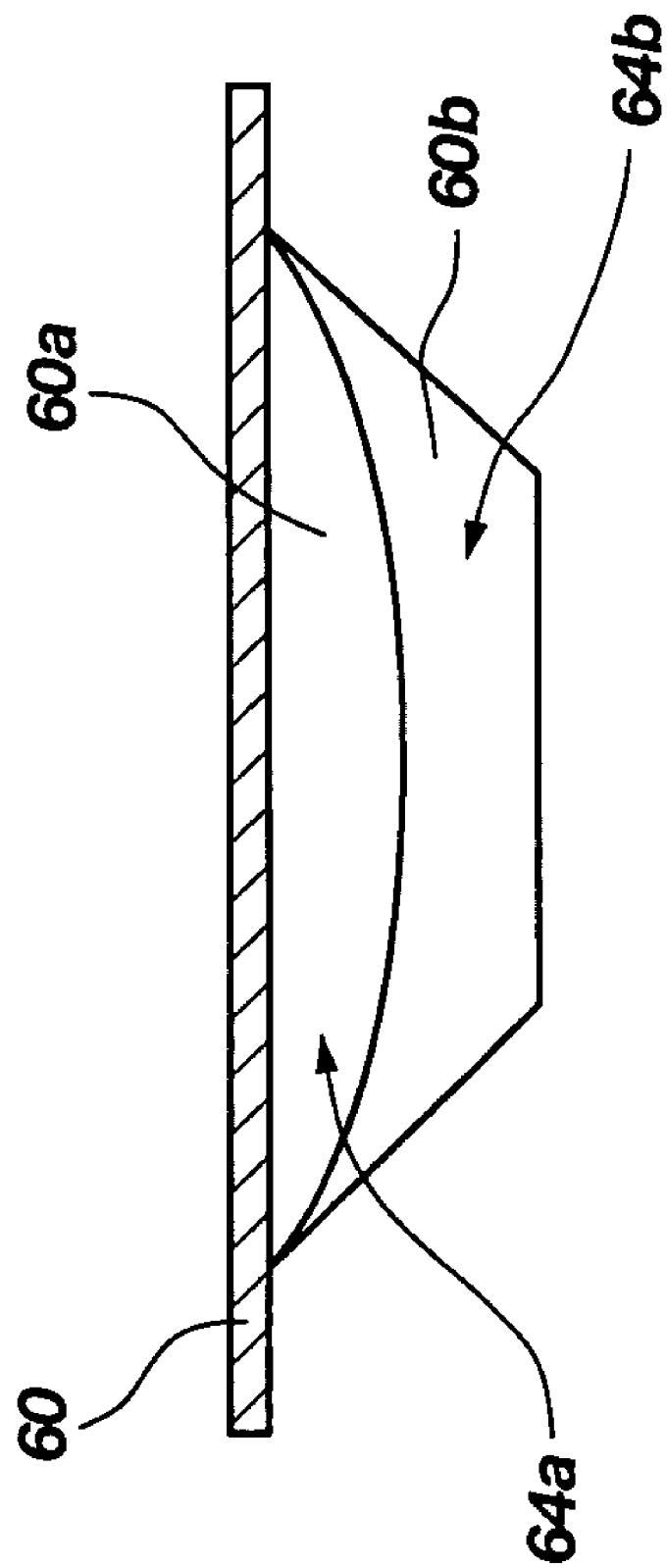
FIG. 3A shows a side cross-sectional view of a single blister made in accordance with the principles of the present invention, having two sub-blisters to isolate two different medicaments.

Turning now to FIG. 3A, there is shown a side cross-sectional view of a single blister 60 made in accordance with the principles of the present invention. The single blister 60 includes a first compartment 60a and a second compartment 60b which keep two medicaments 64a and 64b separated until the blister is lanced. Depending on the lancing mechanism, the medicament could be delivered together or separately. The single blister 60 is particularly advantageous because it can be used in existing inhalers. The blister 60 could also be divided into three compartments if desired to deliver three separate medications.

Figure 3B:
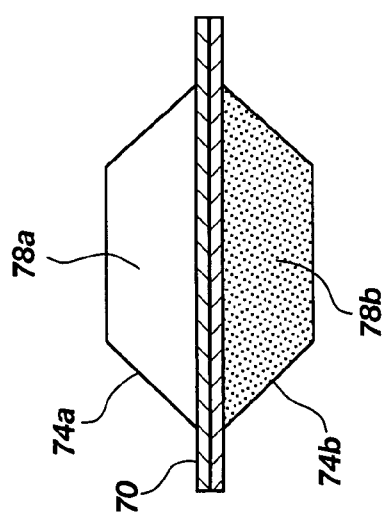
FIG. 3B shows a side cross-sectional view of dual blisters made in accordance with the principles of the present invention.
Figure 3C:
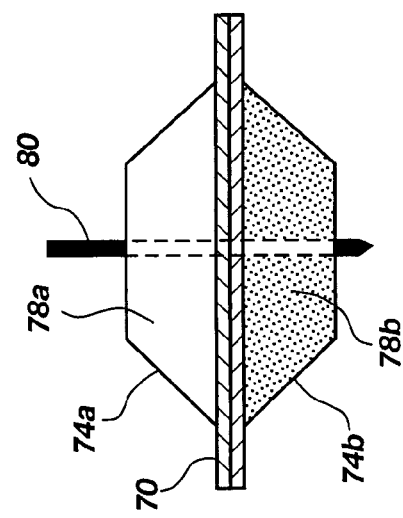
FIG. 3C shows a side cross-sectional view of the dual blisters of FIG. 3B being penetrated by a piercing unit.

FIG. 3B shows a side cross-sectional view of dual blister 70 made in accordance with the principles of the present invention. The dual blister includes a first blister 74a having a first medicament 78a and a second blister 74b having a second medicament 78b. As shown in FIG. 3C, the two blisters can be lanced simultaneously by a piercing mechanism 80, or can be pierced separately. Airflow through the blisters 74a and 74b can then transport the medicament 78a and 78b.

FIGS. 4A and 4B show a blister pack disk 84 in which blisters 88 containing a plurality of medications are all disposed with a common radius on the blister pack disk. These blisters can then be aligned with a pair of channels for delivering the medicament as discussed above.

Figure 5B:
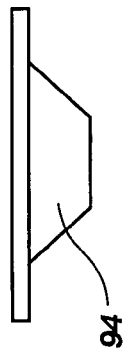
FIGS. 5B and 5C show a side view and an end view of a blister shown in FIG. 5A.
Figure 5C:
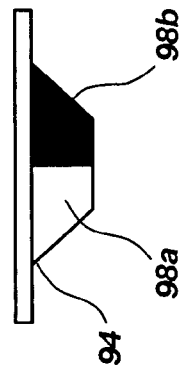
Figure 5A:
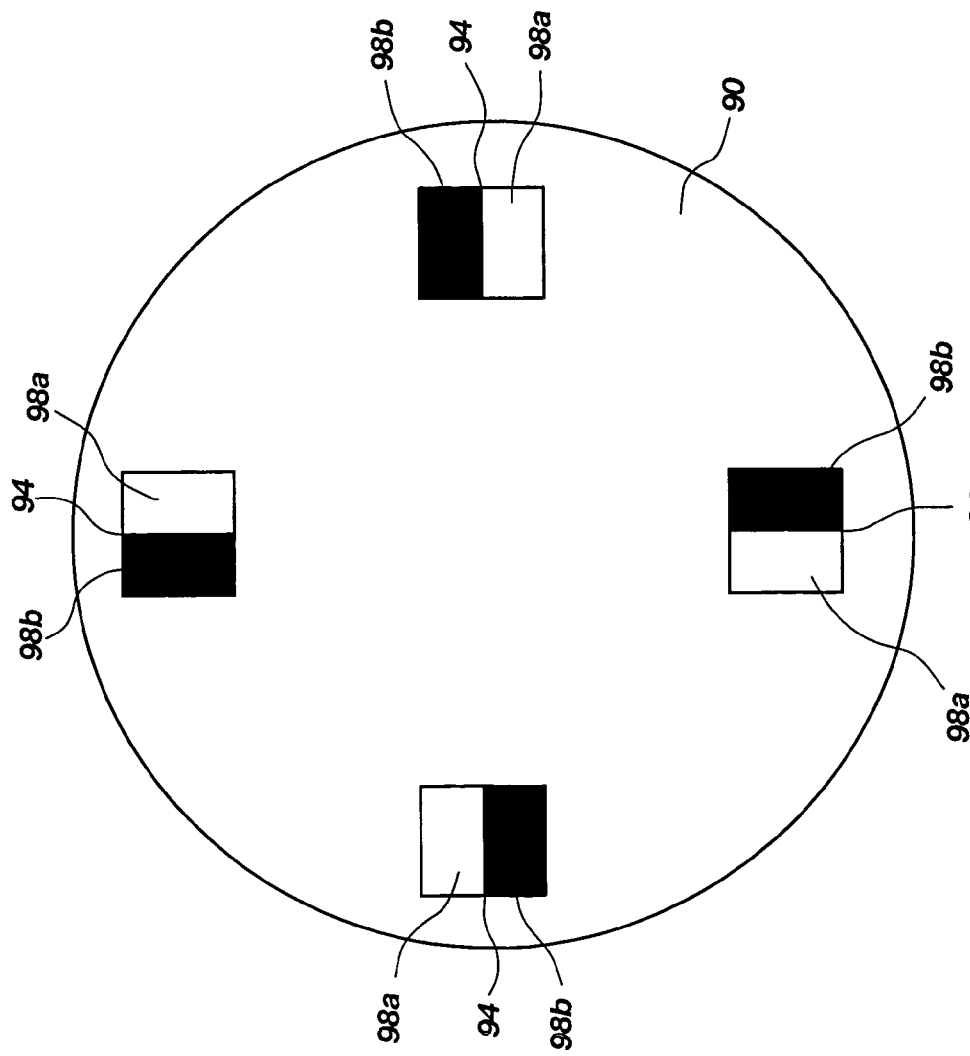
FIG. 5A shows a top view of a different embodiment of a blister pack disk in accordance with the present invention.

FIGS. 5A and 5B show a top view of an alternate embodiment of a blister pack disk 90 and a side view of blister 94 thereof. The disk has a plurality of blisters 94, each of which has two compartments for holding the medicaments 98a and 98b. The side-by-side compartments of the blisters 94 allow the medicament to be accessed through a single airflow channel.

Figure 6B:
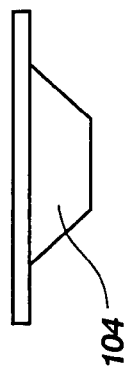
FIG. 6B shows a side view of one type of blister shown in FIG. 6A.
Figure 6C:
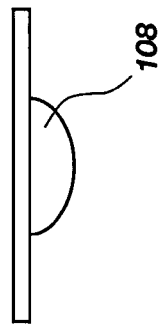
FIG. 6C shows a side view of another type of blister shown in FIG. 6A.
Figure 6A:
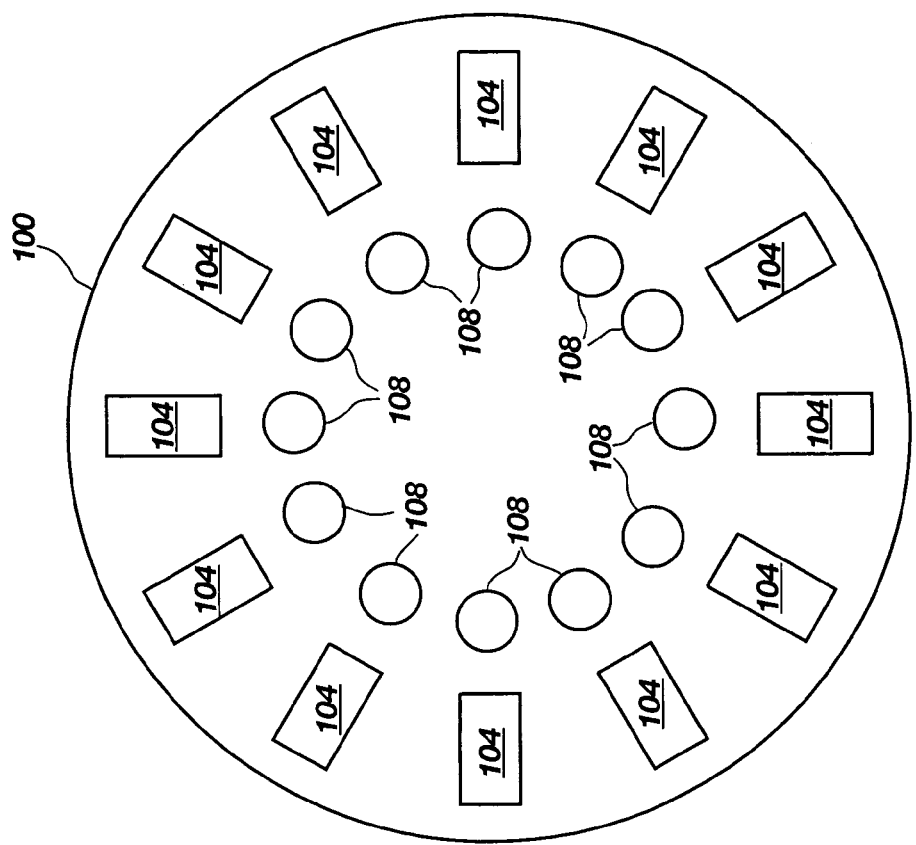
FIG. 6A shows a top view of an alternate configuration of a blister pack disk.

FIGS. 6A through 6C show a top view of an alternate configuration of a blister pack disk, and two side views of the blisters thereof. The blister pack disk 100 has an outer ring of blisters 104 and an inner ring of blisters 108. The outer blisters 104 are filled with a first medicament, and the inner blisters 108 are filled with a second medicament. As shown in FIG. 6A, the inner blisters 108 and outer blisters can be disposed in radial alignment so that they are in-line with a common airflow channel. By controlling the location of the blisters 104, 108 and the configuration of the blisters (see FIG. 6B and FIG. 6C) the entrainment of the medicament in the inhaled air can be controlled.

Figure 7:
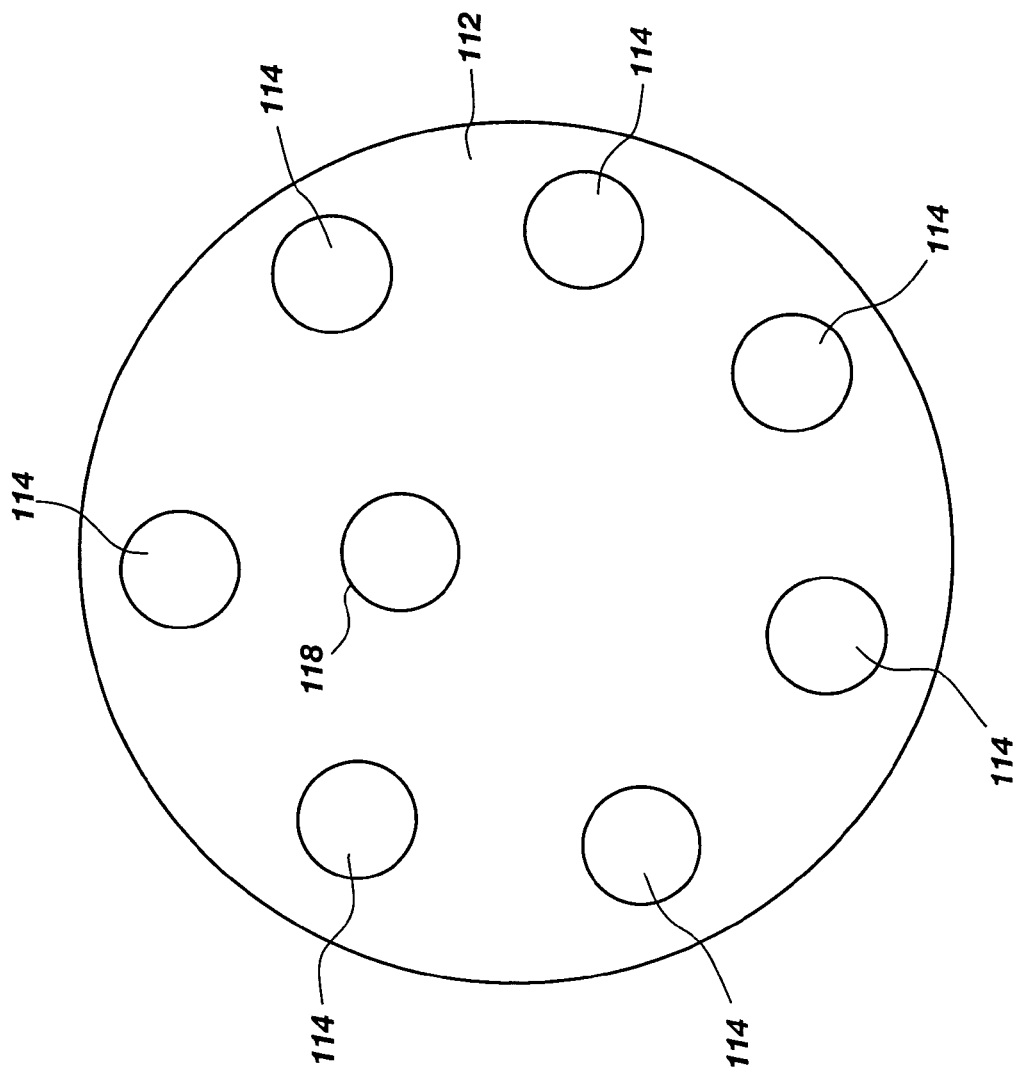
FIG. 7 shows a top view of an alternate configuration of a blister pack disk for two medicaments on different dosing schedules.

FIG. 7 shows a top view of an alternate configuration of a blister pack disk 112. The blister pack disk 112 has a plurality of blisters 114 for containing a first medicament and at least one blister 118 for containing a second medicament. The configuration allows for the delivery of two medicaments having different dosing schedules from a single inhaler. For example, the medicament in blisters 114 can be delivered daily, while the medicament in blister 118 is delivered weekly. This can be achieved without the patient being required to track the different dosing schedules, because the second blister 118 only comes into alignment at the appropriate time.

Figure 8A:
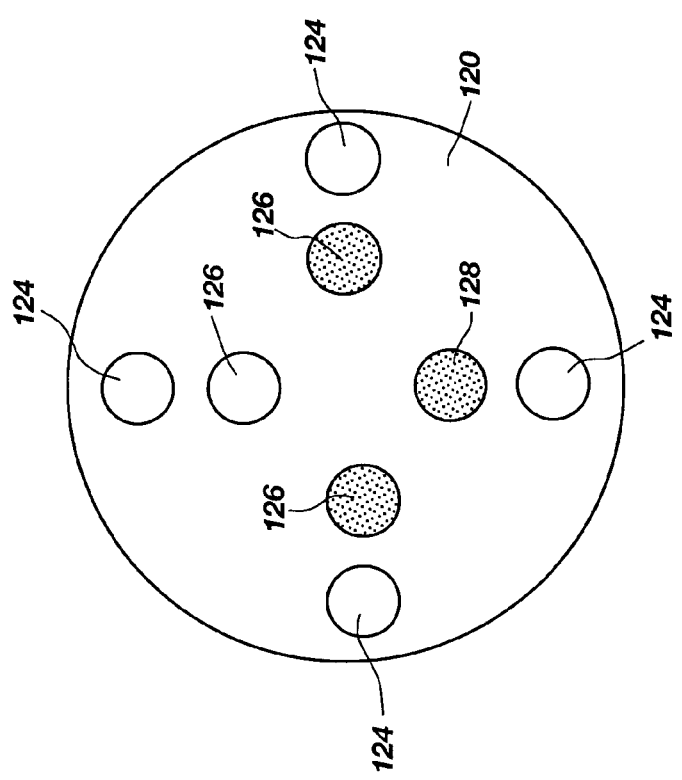
FIG. 8A shows a top view of an alternate configuration of a blister pack disk.
Figure 8B:
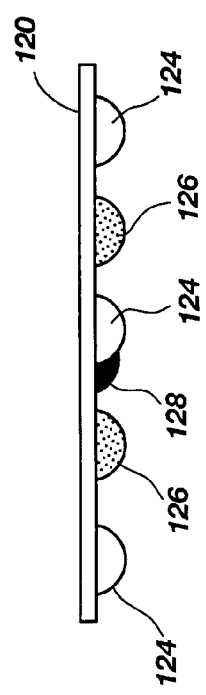
FIG. 8B shows a side view of the blister pack disk of FIG. 8A.

FIGS. 8A and 8B show top and side views of an alternate configuration of a blister pack disk 120. The blister pack disks have a plurality of groups of blisters 124, 126 and 128, with each group being disposed at a different radius from the center of the disk. This allows multiple medications to be delivered on a periodic basis.

Figure 2B:
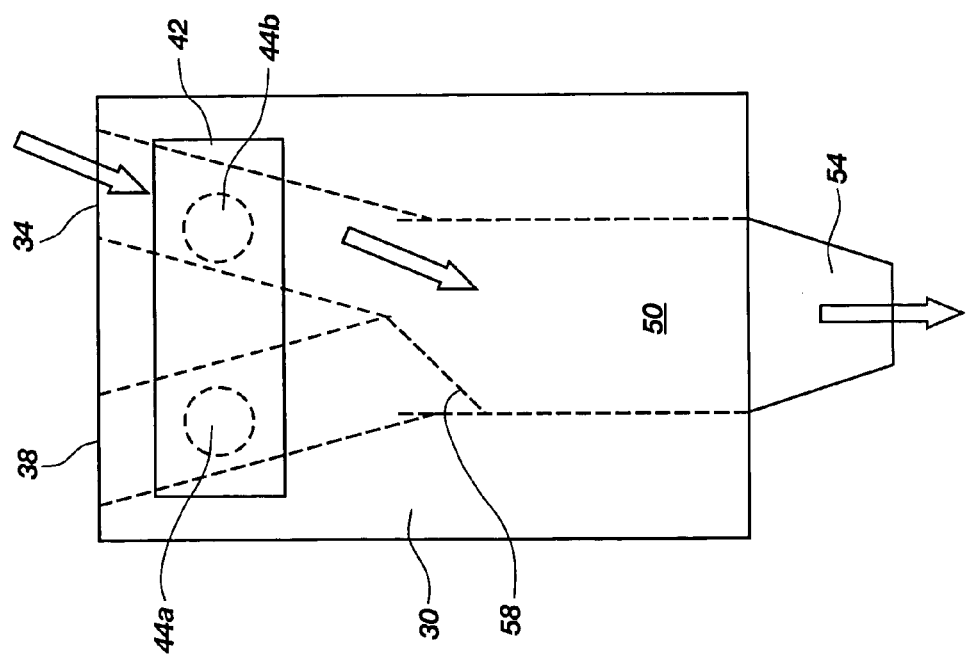
FIG. 2B shows the inhalator of FIG. 2A later in the inhalation cycle.
Figure 9A:
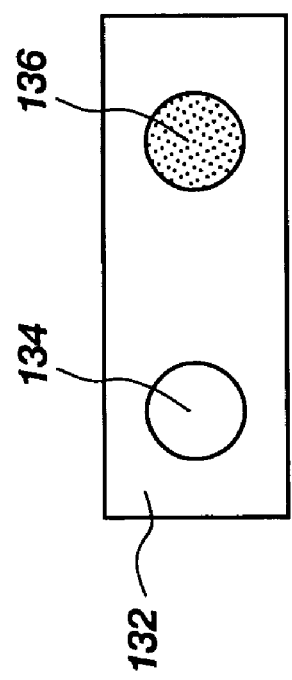
FIG. 9A shows a top view of a blister card made in accordance with the principles of the present invention.
Figure 9B:
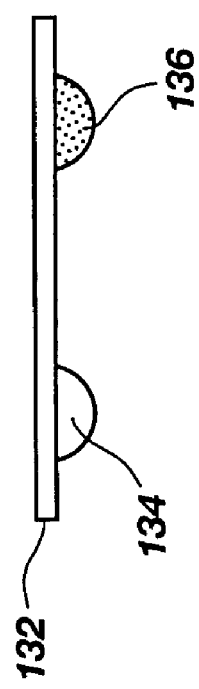
FIG. 9B shows a side view of a blister card of FIG. 9A.

FIGS. 9A and 9B show top and side views of a blister card 132 having a first blister 134 with a first medicament and a second blister 136 with a second medicament disposed side-by-side. The blister card 134 can be inserted in an inhaler which uses separate channels, such as shown in FIGS. 2A and 2B, or disposed in series along a single channel.

Figure 10B:
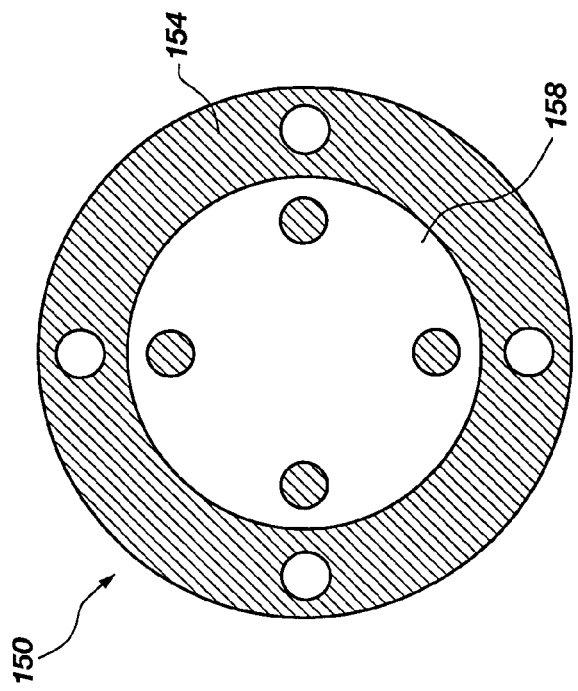
FIG. 10B shows the blister pack disk of FIG. 10A in an assembled state.
Figure 10A:
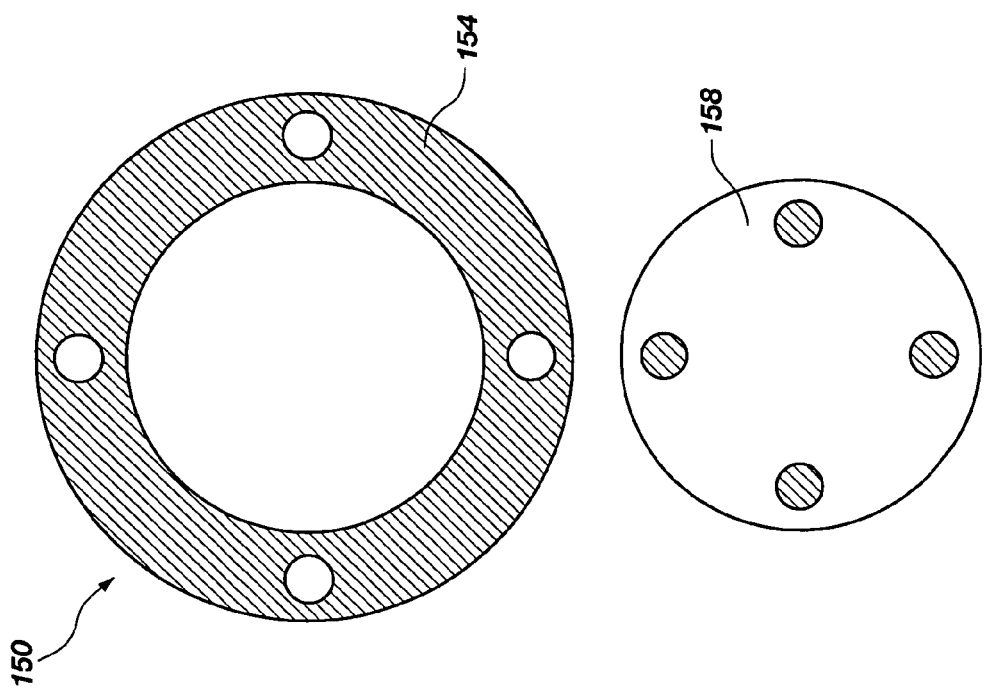
FIG. 10A shows an exploded view of yet another blister pack disk made in accordance with the present invention.

FIG. 10A shows an exploded view of yet another blister pack disk, generally indicated at 150, made in accordance with the present invention. The blister pack disk 150 is formed by an outer disk 154 of blisters containing a first medication, and an inner disk 158 of blisters containing a second medication. Depending on the configuration of the inhaler, the blisters of the outer disk 154 and the inner disk 158 can be in alignment, as shown in FIG. 10B, or can be offset from one another.

FIGS. 11A and 11B show an exploded view of yet another blister card 162. The blister card 162 is formed by a first cross-shaped card 164 and a second cross-shaped card 166. The two cards are then fused or otherwise attached to each other for mounting in an inhaler as shown in FIG. 11A with the medicament in an alternating pattern. By being formed of two parts in accordance with the present invention, the blister can 162 can be formed from numerous different medicament combinations. It will also be appreciated that two disks could be formed so that one disk has a plurality of holes for receiving the blisters of the other disk. Thus, the two disks could be formed separately to prevent contamination between the two medicaments, and then joined to provide a disk having alternating medications in the blisters.

Figure 12B:
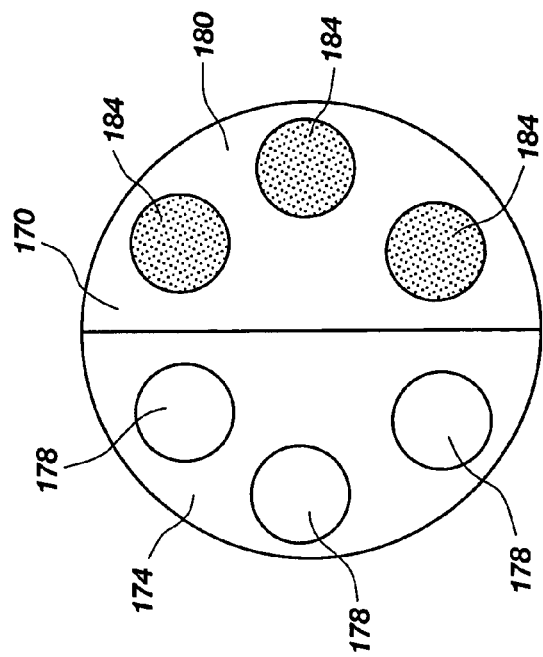
FIGS. 12A and 12B show an alternate embodiment in which two half disks are combined to form a disk having two types of medicament.
Figure 12A:
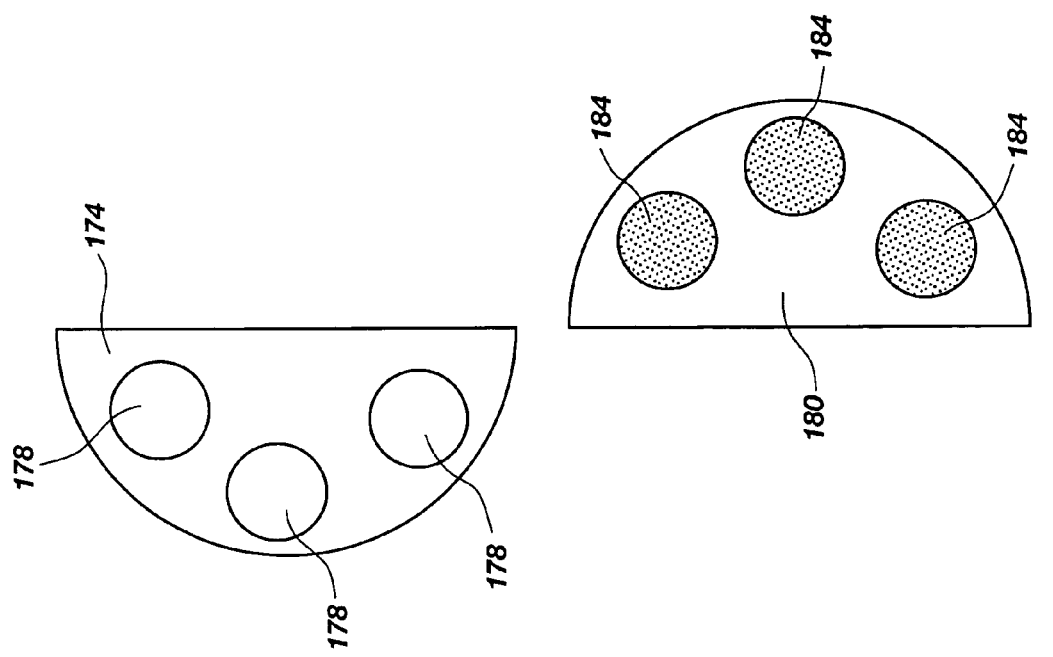

Turning now to FIGS. 12A and 12B, there is shown yet another embodiment of a blister pack disk 170 which is formed by a first half 174 having a plurality of blisters 178 with a first medicament, and a second half 180 having a plurality of blisters 184 having a second medicament. When combined, the halves can form a single disk with opposed blisters having different medicaments. The two halves 174 and 180 can be fused, crimped or attached in numerous different manners which will be readily apparent to those skilled in the art.

Thus there is disclosed an improved combined medicament inhalation drug delivery system for treating and diagnosing respiratory, systemic and topical diseases. Those skilled in the art will appreciate numerous modifications that can be made without departing from the scope and spirit of the present invention. The appended claims are intended to cover such modifications.

What is claimed is:

1. An inhalation blister pack for delivering medicine for inhalation, the blister pack comprising a first blister having a first medicine and a second blister having a second medicine different from the first medicine, the first and second medicines being selected from the group consisting of powders, microcapsules and microspheres, wherein, for dispensing the first and second medicines, the blister pack is loaded into an inhalator, the first and second blisters are pierced simultaneously by a lancing mechanism and the first and second medicines are inhaled by a user.

2. The blister pack for delivering medicine of claim 1, wherein the blister pack comprises a plurality of blisters disposed in a circular pattern.

3. The blister pack for delivering medicine of claim 2, wherein the blister pack comprises a first circular pattern of blisters having a first medicine and a second circular pattern of blisters having a second medicine.

4. The blister pack for delivering medicine of claim 3, wherein the first circular pattern and the second circular pattern are the same diameter.

5. The blister pack for delivering medicine of claim 3, wherein the circular patterns are concentric.

6. The blister pack for delivering medicine of claim 1, wherein at least one of the medicines comprises a medicine for treating respiratory diseases.

7. The blister pack for delivering medicine of claim 1, wherein at least one of the medicines comprises a medicine for oncology diseases.

8. The blister pack for delivering medicine of claim 1, wherein at least one of the medicines comprises a medicine for treating infectious diseases.

9. The blister pack for delivering medicine of claim 1, wherein at least one of the medicines comprises a medicine for treating bone degenerative diseases.

10. The blister pack for delivering medicine of claim 1, wherein at least one of the medicines comprises a medicine for treating neurological degenerative diseases.

11. The blister pack for delivering medicine of claim 1, wherein at least one of the medicines comprises a medicine for pain management.

12. The blister pack for delivering medicine of claim 1, wherein at least one of the medicines comprises a medicine for treating cardiovascular disease.

13. The blister pack for delivering medicine of claim 1, wherein at least one of the medicines comprises a medicine for treating arthritis.

14. The blister pack for delivering medicine of claim 1, wherein at least one of the medicines comprises a medicine for treating hypertension.

15. The blister pack for delivering medicine of claim 1, wherein at least one of the medicines comprises a medicine for treating neurological disorders.

16. A system for delivering medicine for inhalation comprising: a blister pack, the blister pack comprising at least a first blister comprising a first medicine configured for inhalation and selected from the group consisting of powders, microcapsules and microspheres, and at least a second blister comprising a second medicine which is different from the first medicine, configured for inhalation, and selected from the group consisting of powders, microcapsules and microspheres, the first medicine and the second medicine being disposed in separate blisters, a piercing mechanism, and wherein the first blister and second blister are pierced simultaneously by a single piercing mechanism.

17. A system for delivering medicine for inhalation, the system comprising: an inhalator; a blister pack disposed in the inhalator having a lancing mechanism, the blister pack compromising a plurality of first blisters having a first medicine and a plurality of second blisters having a second medicine, wherein the lancing mechanism is arranged to simultaneously pierce a first blister and a second blister.

18. The blister pack for delivering medicine of claim 17, wherein the plurality of first and second blisters are disposed in a circular pattern.

19. The blister pack for delivering medicine of claim 18, wherein the blister pack comprises a first circular pattern of blisters having a first medicine and a second circular pattern of blisters having a second medicine which is different than the first medicine.

20. The blister pack for delivering medicine of claim 19, wherein the first circular pattern and the second circular pattern are the same diameter.

21. The blister pack for delivering medicine of claim 19, wherein the circular patterns are concentric.

22. The blister pack for delivering medicine of claim 17, wherein at least one of the medicines comprises a medicine for treating respiratory diseases.

23. The blister pack for delivering medicine of claim 17, wherein at least one of the medicines comprises a medicine for oncology diseases.

24. The blister pack for delivering medicine of claim 17, wherein at least one of the medicines comprises a medicine for treating infectious diseases.

25. The blister pack for delivering medicine of claim 17, wherein at least one of the medicines comprises a medicine for treating bone degenerative diseases.

26. The blister pack for delivering medicine of claim 17, wherein at least one of the medicines comprises a medicine for treating neurological degenerative diseases.

27. The blister pack for delivering medicine of claim 17, wherein at least one of the medicines comprises a medicine for pain management.

28. The blister pack for delivering medicine of claim 17, wherein at least one of the medicines comprises a medicine for treating cardiovascular disease.

29. The blister pack for delivering medicine of claim 17, wherein at least one of the medicines comprises a medicine for treating arthritis.

30. The blister pack for delivering medicine of claim 17, wherein at least one of the medicines comprises a medicine for treating hypertension.

31. The blister pack for delivering medicine of claim 17, wherein the medicines are selected from at least two of the medicines for treating respiratory diseases, oncology diseases, infectious diseases, bone degenerative diseases, neurological degenerative diseases, pain management, cardiovascular disease and arthritis.

32. The blister pack for delivering medicine of claim 1, wherein the blisters containing different medicines are disposed in an alternating arrangement.

33. The blister pack for delivering medicine of claim 1, wherein the blister pack comprises a first series of blisters containing a first medicine and a second series of blisters containing a second medicine which is different than the first medicine.

34. The blister pack for delivering medicine of claim 33, wherein the second series of blisters is disposed generally parallel to the first series of blisters.

35. The blister pack for delivering medicine of claim 1, wherein one of the at least two blisters containing a first medicine is disposed in contact with another of the at least two blisters containing a second medicine.

36. The blister pack for delivering medicine of claim 16, further comprising a first plurality of blisters containing the first medicine, and a second plurality of blisters containing the second medicine.

37. The blister pack for delivering medicine of claim 17, further comprising a first medicine and a second medicine which is different than the first medicine, and wherein each blister which contains the first medicine is disposed adjacent a blister which contains the second medicine.

38. The blister pack of claim 1, wherein the blister pack comprises a generally planar and continuous surface and wherein the medicine blisters comprise indentations formed in the generally planar and continuous surface.

39. The blister pack of claim 1, wherein the blisters are configured for piercing by a lancet.

40. The blister pack of claim 1, further comprising a first plurality of blisters having a first medicine and a second plurality of blisters having a second medicine, and wherein the first and second plurality of blisters are disposed in a disposed in a single plane.

41. The blister pack of claim 1, wherein the blister pack comprises a first blister pack section having a first group of at least one blister filled with a first medicine and a second blister pack section having a second group of at least one blister filled with a second medicine and wherein the first blister pack section and second blister pack section are configured for assembly into a single blister pack having the first group of blisters and second group of blisters in a single plane.

42. The blister pack of claim 41, wherein the first blister pack section comprises a ring and the second blister pack section comprises a circle or ring smaller than the first blister pack section.

43. The blister pack of claim 41, wherein the first blister pack section comprises a portion of a circle and the second blister pack section comprises a complementary portion of a circle.

44. The blister pack of claim 41, wherein the first blister pack section comprises at least one tab and wherein the second blister pack section comprises a shape complementary to the first blister pack section so as to form a circular or polygonal shaped assembled blister pack.

45. The blister pack of claim 41, wherein the first blister pack section comprises a plurality of tabs extending radially outward from a center and wherein the second blister pack section comprises a shape complementary to the first blister pack section so as to form a circular or polygonal shaped assembled blister pack.

46. The blister pack of claim 1, wherein at least two blisters containing different medicines are configured to be pierced by a single lancet.

47. The blister pack of claim 16, wherein the blister pack comprises a generally planar and continuous surface and wherein the medicine blisters comprise indentations formed in the generally planar and continuous surface.

48. The blister pack of claim 16, wherein the first blister and the second blister are disposed on top of each other.

49. The blister pack of claim 16, wherein the first blister containing said first medicine is disposed in contact with the second blister containing said second medicine.

50. The blister pack of claim 17, wherein the blister pack comprises a first plurality of blisters containing a first medicine and a second plurality of blisters containing a second medicine, and wherein the blisters are arranged in a circular arrangement alternating between at least one of the first plurality of blisters and at least one of the second plurality of blisters and wherein all of the blisters are disposed on a single plane.

51. The blister pack of claim 17, wherein the blister pack comprises a generally planar and continuous surface and wherein the blisters comprise indentations formed in the generally planar and continuous surface.

52. The blister pack of claim 17, wherein the blisters are configured for piercing by a lancet.

* * * * *

UNITED STATES PATENT AND TRADEMARK OFFICE
CERTIFICATE OF CORRECTION

| | | |
|---|---|---|
| PATENT NO. | : 7,931,022 B2 | Page 1 of 1 |
| APPLICATION NO. | : 10/267013 | |
| DATED | : April 26, 2011 | |
| INVENTOR(S) | : Keith A. Johnson, Robert A. Casper and David L. Gardner | |

It is certified that error appears in the above-identified patent and that said Letters Patent is hereby corrected as shown below:

Cover page, item [75] Assignee; should read - Respirics... -

Signed and Sealed this
Twenty-eighth Day of June, 2011

David J. Kappos
*Director of the United States Patent and Trademark Office*